US011654258B2

(12) United States Patent
Gurumoorthy (10) Patent No.: US 11,654,258 B2
(45) Date of Patent: May 23, 2023

(54) SYSTEMS, METHODS, AND DEVICES FOR MEASUREMENT, IDENTIFICATION, AND GENERATION OF SLEEP STATE MODELS

(71) Applicant: StimScience Inc., Berkeley, CA (US)

(72) Inventor: Ram Gurumoorthy, Lafayette, CA (US)

(73) Assignee: STIMSCIENCE NC., Berkeley, CA (US)

( * ) Notice: Subject to any disclaimer, the term of this patent is extended or adjusted under 35 U.S.C. 154(b) by 336 days.

(21) Appl. No.: 17/000,088

(22) Filed: Aug. 21, 2020

(65) Prior Publication Data

US 2022/0054793 A1 Feb. 24, 2022

(51) Int. Cl.
*A61M 21/02* (2006.01)
*A61B 5/24* (2021.01)
(Continued)

(52) U.S. Cl.
CPC ............ *A61M 21/02* (2013.01); *A61B 5/24* (2021.01); *A61B 5/4812* (2013.01);
(Continued)

(58) Field of Classification Search
CPC .. A61B 5/24; A61B 5/293; A61B 5/37; A61B 5/383; A61B 5/4812; A61B 5/4836;
(Continued)

(56) References Cited

U.S. PATENT DOCUMENTS 10,130,788 B2 * 11/2018 Garcia Molina .... A61B 5/7221
2019/0126033 A1 * 5/2019 Pradeep ............. A61N 1/36025
(Continued)

FOREIGN PATENT DOCUMENTS

EP      3669922 A1 * 6/2020 ............. A61B 5/374
WO  2020097618 A1    5/2020
(Continued)

OTHER PUBLICATIONS

Bailey, R. (Jan. 27, 2020). Stages of sleep explained: How brain hormones control your sleep. ThoughtCo. Retrieved Sep. 15, 2022, from https://www.thoughtco.com/stages-of-sleep-explained-4781069 (Year: 2020).*

(Continued)

*Primary Examiner* — Thaddeus B Cox
*Assistant Examiner* — Marc D. Honrath
(74) *Attorney, Agent, or Firm* — Schwegman Lundberg & Woessner, P.A.

(57) ABSTRACT

Provided are systems, methods, and devices for measurement, identification, and generation of sleep state models. Systems include a plurality of electrodes configured to be coupled to a brain of a user and configured to obtain a plurality of measurements from the brain of the user, and an interface configured to obtain the plurality of measurements from the plurality of electrodes. Systems include a processing device comprising one or more processors configured to generate a sleep state model associated with the user, the sleep state model identifying characteristics of a plurality of sleep stages, and further identifying characteristics of transitions between the plurality of sleep stages. Systems include a controller comprising one or more processors configured to generate a control signal based on the sleep state model and the plurality of measurements.

17 Claims, 5 Drawing Sheets

(51) Int. Cl.
*A61B 5/00* (2006.01)
*A61M 21/00* (2006.01)

(52) U.S. Cl.
CPC ............... *A61M 2021/0022* (2013.01); *A61M 2021/0027* (2013.01); *A61M 2021/0072* (2013.01); *A61M 2205/3303* (2013.01); *A61M 2205/502* (2013.01); *A61M 2230/08* (2013.01)

(58) Field of Classification Search
CPC ............... A61B 5/6868; A61B 5/7267; A61M 2021/0022; A61M 2021/0027; A61M 2021/0072; A61M 21/02; A61M 2205/3303; A61M 2205/502; A61M 2230/08
See application file for complete search history.

(56) References Cited

U.S. PATENT DOCUMENTS

| | | | |
|---|---|---|---|
| 2019/0150768 A1* | 5/2019 | Pradeep | G16H 20/70 |
| 2019/0282812 A1* | 9/2019 | Simons | A61N 1/20 |
| 2020/0155061 A1* | 5/2020 | Pradeep | A61B 5/6803 |

FOREIGN PATENT DOCUMENTS

| | | | | |
|---|---|---|---|---|
| WO | WO-2020097618 A1 * | 5/2020 | ........... | A61N 1/0534 |
| WO | WO-2020116796 A1 * | 6/2020 | ............. | A61B 5/369 |

OTHER PUBLICATIONS

European Application Serial No. 21192251.3, Search Report dated Jan. 25, 2022, 10 pgs.

* cited by examiner

SYSTEMS, METHODS, AND DEVICES FOR MEASUREMENT, IDENTIFICATION, AND GENERATION OF SLEEP STATE MODELS

TECHNICAL FIELD

The present disclosure relates to mechanisms and processes directed to measurements associated with brain activity and sleep enhancement.

BACKGROUND

A human brain may include neurons which exhibit measurable electrical signals when active. Accordingly, various measuring modalities, such as electrodes, may be used to measure such electrical activity. The neural activity of neurons may include many a variety of frequency and temporal components. Accordingly, such electrical activity may be measured and represented as a power spectrum in a frequency domain or component features in time domain. However, traditional techniques for measuring electrical activity remain limited in their ability to stimulate such neurons, and more specifically, their ability to determine suitable stimulation parameters for stimulation applied to a user's brain.

SUMMARY

Provided are systems, methods, and devices for measurement, identification, and generation of sleep state models. Systems disclosed herein include a plurality of electrodes configured to be coupled to a brain of a user and configured to obtain a plurality of measurements from the brain of the user, and an interface configured to obtain the plurality of measurements from the plurality of electrodes. Systems include a processing device comprising one or more processors configured to generate a sleep state model associated with the user, the sleep state model identifying characteristics of a plurality of sleep stages, and further identifying characteristics of transitions between the plurality of sleep stages. Systems include a controller comprising one or more processors configured to generate a control signal based on the sleep state model and the plurality of measurements.

In some embodiments, the interface comprises the plurality of electrodes, and wherein the plurality of measurements is neural activity of the user. In various embodiments, the control signal comprises a plurality of stimuli generated based on a plurality of stimulation parameters. According to some embodiments, the controller is further configured to provide the control signal to the brain via the interface and the plurality of electrodes. In some embodiments, the control signal is configured to change a current sleep state of the user. In various embodiments, the plurality of sleep stages comprises a first stage of sleep, a second stage of sleep, a third stage of sleep, and rapid eye movement (REM) sleep. According to some embodiments, the plurality of sleep stages is identified based, at least in part, on the plurality of measurements obtained from the user, and wherein the plurality of stimulation parameters is determined based on the sleep state model. In some embodiments, the control signal includes a plurality of electrical stimuli applied via the plurality of electrodes. In various embodiments, the control signal includes a plurality of auditory or tactile stimuli applied via a sleep environment of the user.

Devices are also disclosed herein that include an interface configured to obtain a plurality of measurements from a brain of a user, a processor configured to generate a sleep state model associated with the user, the sleep state model identifying characteristics of a plurality of sleep stages, and further identifying characteristics of transitions between the plurality of sleep stages, and a controller comprising one or more processors configured to generate a control signal based on the sleep state model and the plurality of measurements.

In some embodiments, the interface comprises a plurality of electrodes, and wherein the plurality of measurements is neural activity of the user. In various embodiments, the control signal comprises a plurality of stimuli generated based on a plurality of stimulation parameters, and wherein the controller is further configured to provide the control signal to the brain via the interface and the plurality of electrodes. According to some embodiments, the control signal is configured to change a current sleep state of the user, and wherein the plurality of sleep stages comprises a first stage of sleep, a second stage of sleep, a third stage of sleep, a fourth stage of sleep, and rapid eye movement (REM) sleep. In some embodiments, the plurality of sleep stages is identified based, at least in part, on the plurality of measurements obtained from the user, and wherein the plurality of stimulation parameters is determined based on the sleep state model.

Also disclosed herein are methods that include receiving, via an interface coupled to a brain of a user, a plurality of measurements from the user, identifying, using one or more processors of a processing device, based, at least in part, on the plurality of measurements, a plurality of sleep stages of the user, generating, using one or more processors of the processing device, a sleep state model associated with the user, the sleep state model identifying characteristics of each of the plurality of sleep stages, and further identifying characteristics of transitions between the plurality of sleep stages.

In some embodiments, the interface comprises a plurality of electrodes, wherein the plurality of measurements is neural activity of the user, the control signal comprises a plurality of stimuli generated based on a plurality of stimulation parameters, and the controller is further configured to provide the control signal to the brain via the interface and the plurality of electrodes. In various embodiments, methods further include generating, using one or more processors of a controller, a control signal based on the sleep state model and the plurality of measurements, wherein the control signal changes a current sleep state of the user, and wherein the plurality of sleep stages comprises a first stage of sleep, a second stage of sleep, a third stage of sleep, a fourth stage of sleep, and rapid eye movement (REM) sleep. According to some embodiments, the plurality of sleep stages is identified based, at least in part, on the plurality of measurements obtained from the user, and wherein the plurality of stimulation parameters is determined based on the sleep state model. In some embodiments, the control signal includes a plurality of electrical stimuli applied via a plurality of electrodes. In various embodiments, the control signal includes a plurality of auditory or tactile stimuli applied via a sleep environment of the user.

This and other embodiments are described further below with reference to the figures.

DETAILED DESCRIPTION OF EXAMPLE EMBODIMENTS

Reference will now be made in detail to some specific examples of the invention including the best modes contemplated by the inventors for carrying out the invention. Examples of these specific embodiments are illustrated in the accompanying drawings. While the present disclosure is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In addition, although many of the components and processes are described below in the singular for convenience, it will be appreciated by one of skill in the art that multiple components and repeated processes can also be used to practice the techniques of the present disclosure.

In the following description, numerous specific details are set forth in order to provide a thorough understanding of the present invention. Particular embodiments of the present invention may be implemented without some or all of these specific details. In other instances, well known process operations have not been described in detail in order not to unnecessarily obscure the present invention.

As discussed above, components, such as electrodes, may be used to measure electrical activity in a brain, as well as provide stimulation to the brain. Traditional techniques remain limited in their ability to stimulate such neurons because they are not able to determine suitable stimulation parameters for stimulation applied to a user's brain. For example, traditional implementations of electrodes might be limited to surface or scalp implementations, and may be limited in sensitivity to signal, spectrum, and localization when obtaining measurements, and determining suitable stimulation protocols, as will be discussed in greater detail below.

Moreover, traditional neuronal signal modeling mechanism have significant limitations. Available brain signal decoding mechanisms only directly measure simple signatures of behavior like the increase or decrease of alpha desynchronization. However, such techniques do not estimate a real state to be modified. For example, alpha desynchrony may just be overall arousal state. Other traditional systems like uni-variate and uni-modal systems are not able to accurately model complicated neural systems. Such simple models do not account for cross impacts of sub-systems or multiple modalities of measurements, and are not able to detect or identify various states or parameters that are to be monitored and controlled. Some other traditional techniques are open loop techniques with electrical or magnetic stimulation of different regions with manual tuning and long term behavior tracking that are not only inefficient but can also be erroneous. Such techniques may result in over-stimulation and/or under-stimulation.

As will be discussed in greater detail below, various embodiments disclosed herein provide the ability to obtain measurements and provide stimulation via intracranial modalities, and in conjunction with surface or scalp level modalities. Such intracranial implementations facilitate the measurement and acquisition of electrocortical data, as may be consistent with electrocorticography (ECoG) or intracranial electroencephalography (iEEG), to develop brain state and functional models. The use of such intracranial implementations enables the increase of accuracy of brain state and functional models, as well as the generation and estimation of additional new states that might not be observable and predictable by scalp level modalities alone. Moreover, such intracranial implementations may further enable the increased accuracy of generation of stimulation parameters, such as field strength of actuators as well as a position of actuators. In addition, various embodiments may include other measurement modalities such as MEG, fMRI, NIRS, respiration, heart rate, electrooculography (EOG), temperature, body movements, oximetry in estimating the user brain state and developing the brain state and functional models. The user brain state assessment can also use self-reported questionnaires (like alertness, refreshedness, sleepiness, anxiety, cognitive state assessments like PANAS) and behavioral tasks that assess attention, motor, vigilance, emotion/mood, memory and such functional states. These questionnaires and tests could be administered one time or multiple times before and after specific events of interest (such as stimulation, sleep).

Various embodiments disclosed herein provide the ability to obtain measurements from a brain of a user, and generate various brain state parameters characterizing one or more features of at least one brain state of the user, as well as various models of the brain of the user. Such brain state parameters implemented in conjunction with the generated models provide a closed loop adaptive therapeutic system that may obtain measurements, generate a generalized or user specific functional and/or structural model of the brain, estimate desired brain signatures and states, generate control signals to obtain such desired brain states, and obtain additional measurements if appropriate to continuously adjust the signals and the models. In this way, various embodiments disclosed herein provide therapeutic and cognitive modulation techniques that are adaptive closed loop techniques that provide, among other things, desired modulations with increased efficiency and efficacy.

As similarly discussed above, at least some of the measurements may be acquired using intracranial data obtained from intracranial electrodes. Such electrodes implanted within the cortical tissue may be configured to have high sensitivity with respect to signal amplitude, frequency spectrum, as well as signal localization. Accordingly, such ECoG data may be utilized to develop and generate brain parameters associated with brain states as well as functional and structural models, as discussed in greater detail below with reference to at least FIG. 2. More specifically, the intracranial data be used to generate and identify brain states as well as functional and structural models, and may also be used to generate control signals. Furthermore, such intracranially obtained data may include both normal and pathological episode data thus providing a comprehensive representation of a user's neural activity. These enhanced models obtained from users can also help identify general structural/functional models for other users and groups.

Furthermore, various embodiments disclosed herein provide enhancements in a user's ability to enter sleep and advance through stages of sleep. As will be discussed in greater detail below a user may have numerous different stages of sleep that are each characterized by a dominant rhythm or temporal patterns of neural activity. Embodiments disclosed herein provide a user with customized stimulation that is configured to help the user transition from one state to another. More specifically, a sleep state model may be generated and used to determine and apply particular stimuli to the user to aid the user with transitioning to a next sleep stage. In this way, the user's advancement and progression through stages of sleep is improved, and such control over transitions between stages may be dynamically modified and updated based on changes in the user's behavior.

Additional details will be discussed in greater detail below with reference to components of systems disclosed herein as well as brain state and functional model generation, stimulation, closed loop control, and prosthetic control. Accordingly, the implementations of intracranial electrodes discussed above may be implemented in conjunction with systems as disclosed in FIG. 1, and methods as disclosed in FIGS. 2, 3, and 4. For example, such electrodes may be implemented as part of interface 102 discussed in greater detail below, and acquired data may be used in accordance with methods 200, 300, and 400 discussed below.

Figure 1:
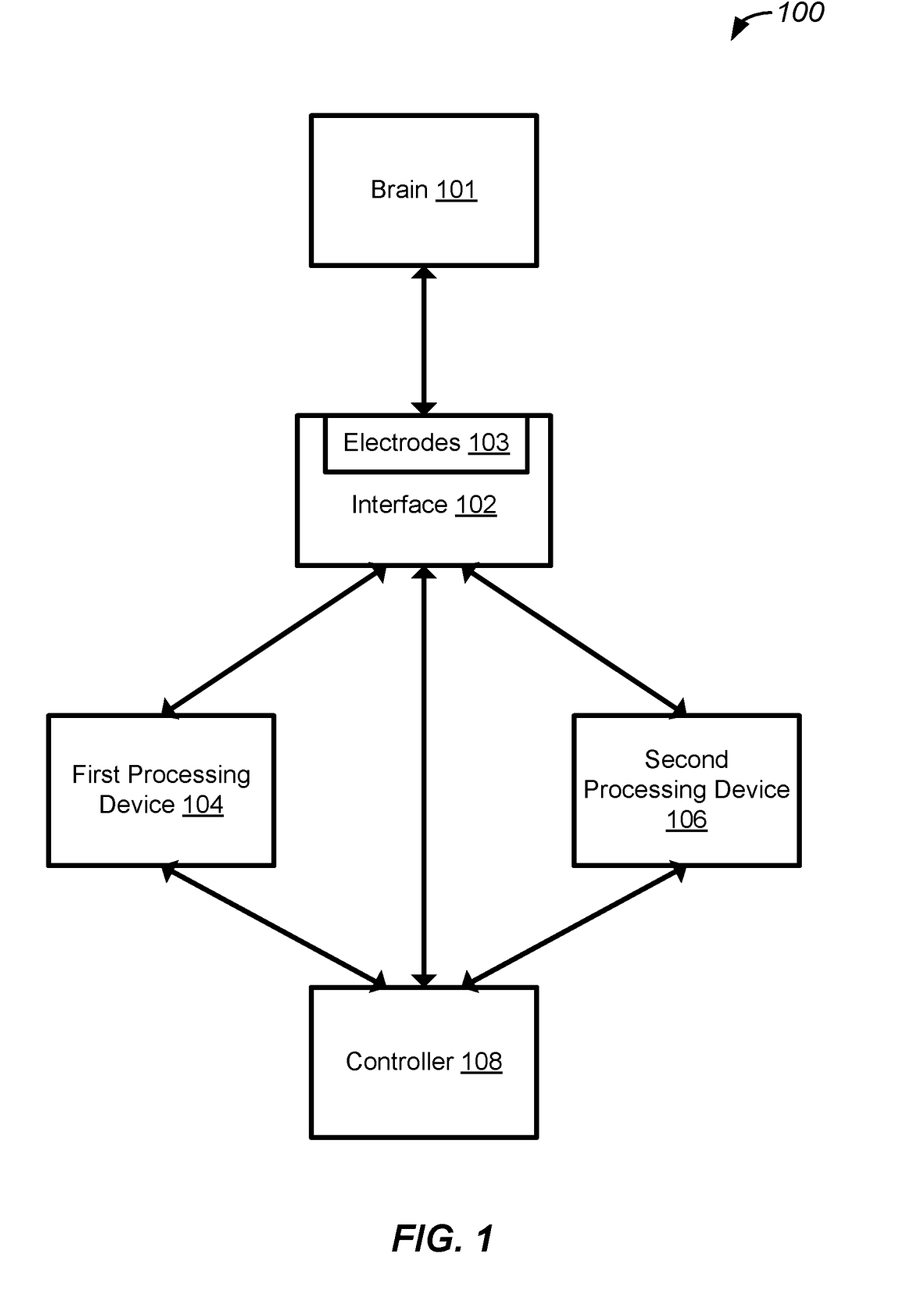
FIG. 1 illustrates an example of a system for providing closed loop control in treatments and cognitive enhancements, configured in accordance with some embodiments.

FIG. 1 illustrates an example of a system for providing closed loop control in treatments and cognitive enhancements, configured in accordance with some embodiments. In some embodiments, system 100 includes an interface, such as interface 102. In various embodiments, interface 102 is a brain interface that is configured to be coupled with a brain, such as brain 101. As will be discussed in greater detail below, such coupling may provide bidirectional communication, or may be used for various sensing modalities. In some embodiments, interface 102 includes various electrodes, such as electrodes 103, which may be included in an electrode array. Such electrodes may be included in a scalp potential electroencephalogram (EEG) array, may be deep brain stimulation (DBS) electrodes such as electrodes used with intracranial electroencephalography, or may be an epidural grid of electrodes. In other examples, interface 102 may include optogenetics mechanisms for monitoring various neuronal processes (central or peripheral). In other examples, interface 102 may include MEG, fMRI, NIRS, respiration, heart rate, electrooculography (EOG), temperature, body movements, oximetry devices. Mechanisms may be used to make various measurements and acquire measurement signals corresponding to neural activity. As used herein, neural activity may refer to spiking or non-spiking activity/potentiation.

In various embodiments, such measured signals may be electrical signals derived based on neural activity that may occur in cortical tissue of a brain. Such measurements may be acquired and represented in a time domain and/or frequency domain. In this way, neural activity may be monitored and measured over one or more temporal windows, and such measurements may be stored and utilized by system 100. In various embodiments, such neural activity may be observed for particular regions of cortical tissue determined, at least in part, based on a configuration of interface 102. In one example, this may be determined based on a configuration and location of electrodes included in interface 102 and coupled with the brain.

According to some embodiments, one or more components of interface 102 are configured to provide stimuli to the brain coupled with interface 102. For example, one or more electrodes included in interface 102 may be configured to provide electrical stimuli to cortical tissue of the brain. As discussed above, such electrodes may be implemented utilizing one or more of various modalities which may be placed on a user's scalp, or implanted in the user's brain.

As will be discussed in greater detail below, such actuation and stimuli provided by interface 102 may be of many different modalities. For example, stimuli may be aural, visual, and/or tactile as well as being electrical and/or magnetic, or any suitable combination of these. Accordingly, interface 102 may further include additional components, such as speakers, headphones, bone-conducting speakers, lights, display screens, and mechanical actuators that are configured to provide one or more of aural, visual, and/or tactile stimuli to a user. In this way, any suitable combination of different modalities may be used. For example, a combination of electrical and aural stimuli may be provided via interface 102. Further still, interface 102 may include different portions corresponding to signal acquisition and stimuli administration. For example, a first portion of interface 102 may include electrodes configured to measure neural activity, while a second portion of interface 102 includes speakers configured to generate aural stimuli.

In some embodiments, interface 102 further includes one or more dedicated processors and an associated memory configured to obtain and store the measurements acquired at interface 102. In this way, such measurements may be stored and made available to other system components which may be communicatively coupled with interface 102.

System 100 further includes first processing device 104 which is configured to generate brain state parameters that may characterize and identify features of brain states and generate estimations of brain state signatures. In various embodiments, a brain state may refer to one or more identified patterns of neural activity. Accordingly, such brain states may be one or more identified patterns, such as oscillation or fluctuation of activity at a particular frequency band, such as low oscillatory behavior as well as delta, theta, alpha, beta, and gamma waves. Furthermore, such brain states may be identified based on coupling between patterns of neural activity. For example, a brain state may be identified based on oscillation or fluctuation of activity at a particular frequency band, and an increase of activity in another. Other brain states may correspond to phase resets in prefrontal and cingulate areas. Phase resets may correspond to coherent activity in widespread cortical regions and impact timing of neuronal activity. Activity patterns in the prefrontal cortex can be monitored, identified, and controlled for associations with particular behaviors including goal directed behavior. Neuronal synchronization and desynchronization may be detected and managed using closed loop control based on intelligent and continuously adaptive neurological models. As will be discussed in greater detail below, such identification may be implemented based, at least in part, on various parameters, such as observers and estimators.

Accordingly, first processing device 104 is configured to generate one or more particular observers and/or estimators that may form the basis of identification and estimation of brain states, described in greater detail below. As discussed above, first processing device 104 may be configured to generate deterministic and stochastic observers and estimators of brain states based on acquired measurements. Such deterministic observers may provide robustness to exogenous disturbances, while such stochastic estimators may provide robustness regarding noise. For example, first processing device 104 may be configured to implement linear and nonlinear observation and estimation modalities such as luenberger, kalman, sliding mode, and benes filters. The application of such observation and estimation modalities may be used to generate and infer one or more parameters associated with brain states. For example, such parameters may identify aspects of particular brain states, such as an oscillation or resonance frequency, specific temporal patterns like event potentials or spindle/k-complex sequences, as well as a coupling and/or weighting factor associated with one or more other brain states. In a specific example, a condition of Schizophrenia may be modeled as a pair of oscillators, each being an oscillating neural pattern, and first processing device 104 may be configured to identify and determine resonance frequencies and coupling factors associated with the oscillators based on the previously described acquired measurements. In various embodiments, such coupling factors characterize coupling between individual degrees of freedom of each modeled oscillator. Accordingly, such coupling factors may be configured to identify one or more features of coupling between modeled neural oscillators, such as one or more modes.

Thus, according to various embodiments, first processing device 104 may be configured to implement direct and indirect state signature estimation. First processing device 104 may also be configured to implement brain system model parameter identification and adaptation. Furthermore, first processing device 104 may also be configured to generate an estimation of the stability of underlying hidden states, as well as noise estimation and rejection in underlying measurements. In various embodiments, first processing device 104 may also be configured to implement cognitive relevance based measurement window sizing. Accordingly, measurement windows may be sized based on cognitive relevance measures, and may be sized dynamically.

In some embodiments, first processing device 104 is configured to implement baseline estimation and removal which may enhance sensitivity regarding signatures/events. As discussed above, neural activity may be measured and represented in a time domain and/or a frequency domain. In one example, when represented in a frequency domain, the neural activity may be represented as a power spectrum that follows a plot that is logarithmic or non-linear. Accordingly, in various embodiments, first processing device 104 is configured to implement one or more curve-fitting modalities to estimate a baseline of the plot, and remove such baseline to provide a more accurate representation of more granular features of the measured signal. Such granular features may be represented with greater accuracy, and be used to identify parameters of brain states with greater accuracy.

First processing device 104 may also be configured to implement learning estimator models that learn state changes and estimate them. Such learning estimator models may also learn changing system parameters, and estimate the improvement/retrograde of behavioral/functional responses.

As similarly discussed above, observers and estimators may be used to identify and/or infer state signatures and parameters associated with brain states. For example, examples of brain state signatures may include certain lower frequency oscillations mediated with or coupled to higher frequency oscillations (delta to alpha, alpha to gamma, theta to mu, alpha to high frequency band) that correspond with various levels of cognitive ability and various types of cognitive conditions, to detect and identify signatures indicative of particular types of cognitive performance or cognitive conditions.

According to various embodiments, slow wave coupled spindle synchrony during sleep may be used as a signature of memory retention and consolidation. In particular embodiments, a closed loop control system may be configured to monitor and improve slow wave coupled spindle synchrony. In another example, first processing device 104 is configured to detect multiplexed parallel delta to theta, alpha to beta, delta/theta/alpha to high-frequency-band coupling to identify a signature of working memory. In yet another example, first processing device 104 is configured to monitor and/or control a baseline rate of exponential decay in a spectral composition of neural activity, as well as deviations from the baseline to identify and predict a cognitive and arousal state, such as an inhibitory or excitatory state. In various embodiments, first processing device 104 may also be configured to monitor beta synchronization or desynchronization to identify a signature of motor activity intent. In yet another example, first processing device 104 may be configured to estimate ratios of various spectral band performance like slow wave to high beta, delta to high beta, slow wave to beta to identify signatures of sleep quality during sleep. In this way, any number of brain states and associated signature and parameters may be identified and estimated by first processing device 104. In some embodiments, first processing device 104 may be configured to identify an "activity silent" mode associated with a user in which a measure of activity is measured and tracked as a mental state shift indicator.

System 100 further includes second processing device 106 which is configured to generate functional and structural models of the brain coupled with interface 102. In various embodiments, second processing device 106 is further configured to provide brain functional model identification and adaptive learning, as well as brain structural models that model structures of the brain and are configured to implement adaptive learning. In various embodiments, second processing device 106 is communicatively coupled with interface 102, first processing device 104, as well as controller 108 discussed in greater detail below. Accordingly, second processing device 106 may receive input signals from one or more other system components and utilize such inputs to form and/or update functional and structural models of the brain coupled with interface 102. In various embodiments, second processing device 106 may also be configured to pre-process inputs received from interface 102 and first processing device 104 to generate one or more composite inputs.

In various embodiments, second processing device 106 is configured to generate functional input-output univariate and multivariate models that may be configured to approximate at least some of the input-output behavior of the brain coupled with interface 102 described above. In some embodiments, second processing device 106 is also configured to implement adaptive learning brain models that may iteratively update and improve the functional model of the brain that has been constructed.

In some embodiments, second processing device 106 is configured to implement deep/machine learning and data mining based system models. Accordingly, second processing device 106 may be configured to implement one or more artificial neural networks that may be configured to model tasks or cognitive functions of the brain. Such neural networks may be implemented in a hierarchical manner. Moreover, such neural networks may be trained based on signals received from other components of system 100. For example, models may be trained based on inputs provided to interface 102 from controller 108 and outputs measured via interface 102 as well as observers and estimators generated by first processing device 104.

In this way, input and output activity within system 100 may be used, at least in part, to construct functional and structural models represented by second processing device 106. More specifically, the artificial neural networks created by second processing device 106 may be modified and configured based on activity of the human brain. In this way, the artificial neural networks created by second processing device 106 may be specifically configured based on behaviors and processing patterns of the human mind.

In various embodiments, second processing device 106 is further configured to implement system identification, dimensional modeling, and dimension reduction to identifying preferred models. Such neural networks could be used to develop a reduced state representation model of the system that could accurately capture the functional behavior and yet be robust to individual variations. Furthermore, second processing device 106 may be configured to implement identification of one or more brain states to be controlled, as may be determined based on actuation sensitivity and efficacy. In various embodiments, second processing device 106 is configured to implement identification of the most sensitive brain states to be measured. Such identification may identify the most sensitive and granular measurement that identifies the brain state changes. In some embodiments, second processing device 106 is configured to implement multi-input, multi-output measurement and actuation. In some embodiments, second processing device 106 is further configured to multi-time scale modelling (to capture the slow system and fast system dynamic accurately). In various embodiments, second processing device 106 is also configured to implement one or more neural net basis functions that may be configured and or generated based on activity of the brain. For example, such functions may include spike functions, multi-input-coevolution triggered firing (such as coherence, synchrony, coupling, correlation of two waveforms triggering a cell firing).

While first processing device 104 and second processing device 106 have been described separately, in various embodiments, both first processing device 104 and second processing device 106 are implemented in a single processing device. Accordingly, a single processing device may be specifically configured to implement first processing device 104 and second processing device 106.

As will also be discussed in greater detail below, first processing device 104 and second processing device 106 may be specifically configured to generate one or more sleep state models for a user. Accordingly, first processing device 104 and second processing device 106 are configured to generate one or more data structures that are configured identify and represent different stages of sleep of the user, as well as characteristics and patterns of neural activity for each stage. The characteristics and patterns of neural activity may be predetermined based on default values, or may be generated based on a learning or observation phase. Accordingly, during such a learning or observation phase, neural activity of the user may be monitored, and data values representing each sleep state be identified and recorded for each detected sleep stage. In some embodiments, the sleep stages may be detected based on predetermined or default baselines which may be retrieved from a database or may be averaged from other users. Accordingly, such predetermined data may be used to aid in the detection of sleep stages, and specific data values of the user's neural activity may be recorded for each sleep stage. In some embodiment, the identification of sleep stages may be implemented using one or more of the algorithms and parameters discussed above.

System 100 further includes controller 108 configured to implement and control closed loop control of treatments and cognitive enhancements. In various embodiments, controller 108 is communicatively coupled with interface 102, first processing device 104, and second processing device 106. Accordingly, controller 108 is configured to received inputs from various other system components, and generate outputs based, at least in part on such inputs. As will be discussed in greater detail below, such outputs may be used to provide actuations to the brain coupled with interface 102. For example, outputs generated by controller 108 may be used to stimulate the brain via one or more components of interface 102. In this way, controller 108 may provide stimuli to the brain via interface 102, may receive measurements, parameter information, and model information via other components such as first processing device 104 and second processing device 106, and may generate updated stimuli based on such received information.

Thus, according to some embodiments, controller 108 is configured to implement multi-input, multi-output feedback control. Controller 108 may also be configured to implement loop shaping optimized feedback control. In a specific example, controller 108 is configured to implement model reference adaptive control. Furthermore, controller 108 may be configured to implement cognitive enhancement trajectory control. In various embodiments, controller 108 is configured to implement enhanced control in which one or more parameters of a treatment may be enhanced by increasing its efficiency and/or effect. For example, an input or stimulation may be reduced to implement a same enhancement, a duration of stimulations may be reduced but still reach desired improvement, and a path of recovery may be made more efficient. In this way, an amount of stimulation, which may be a combination of amplitude and duration, may be reduced while still obtaining a desired effect, thus increasing the efficacy of the treatment and reducing overstimulation. In various embodiments, controller 108 is configured to implement a genetic algorithm to identify a particular stimulation pathway that reduces an amount of stimulation. For example, the frequency or combination of frequencies of stimulation may be modified to obtain a desired effect such that the frequency/frequencies of stimulation could be based on functional brain models and/or individual-specific resonant frequencies.

In some embodiments, controller 108 is configured to implement combined control of pharmacological and stimulation inputs. Accordingly, controller 108 may be configured to modify stimulation inputs based on an expected effect of one or more pharmacological agents that may be administered in conjunction with the stimulation. In this way, controller 108 may modify and control administration of stimuli via interface 102 based on an identified pharmacological regimen. In various embodiments, controller 108 is configured to implement game theoretic strategy-based treatments. In some embodiments, controller 108 is configured to implement real time measurement/estimation and control.

In various embodiments, controller 108 is configured to receive a reference signal which may be used, at least in part, to generate or modify the stimuli provided via interface 102. In various embodiments, the reference signal may be a previously determined signal or pattern that may represent a reference level or pattern of neural activity. In some embodiments, the reference signal may be generated based on a "negative" model. In a specific example, such a negative model may be a functional and/or structural model that is generated based on a reverse or inversion of one or more of the models created and stored by second processing device 106. Accordingly, such a negative model may be generated by second processing device 106, and the reference signal may be generated by second processing device 106 and received at controller 108.

In some embodiments, system 100 may be configured to provide a toolbox configured to support estimation, modeling, and control. In another example, system 100 may be configured to provide a bio operating system (BoS) framework for biological measurement and an actuation control platform. In some embodiments, system 100 may be configured to provide task specific cognitive enhancements, such as FAA monitoring agents, and fighter pilot related tasks.

System 100 and its respective components may be implemented in a variety of contexts. For example, system 100 may be implemented in a clinical setting that may include an examination room, an operating room, or an emergency room. Moreover, system 100 may be implemented in a user's home thus providing in-home monitoring, diagnostic, and treatment. Furthermore, portions of system 100 may be implemented in a first location while other portions are implemented in a second location. For example, interface 102 may be located at a user's home, while first processing device 104, second processing device 106, and controller 108 are implemented remotely, as may be the case when implemented at a hospital.

Furthermore, system 100 may be implemented across multiple users. For example, system 100 may include multiple interfaces that are coupled with multiple brains. In this way, measurements may be made from multiple users, and stimuli may be provided to multiple users. In one example, measurements from a first user may be used to generate and provide stimuli to a second user. In this way, synchronization of at least part of a brain state may be implemented across multiple users.

Figure 2:
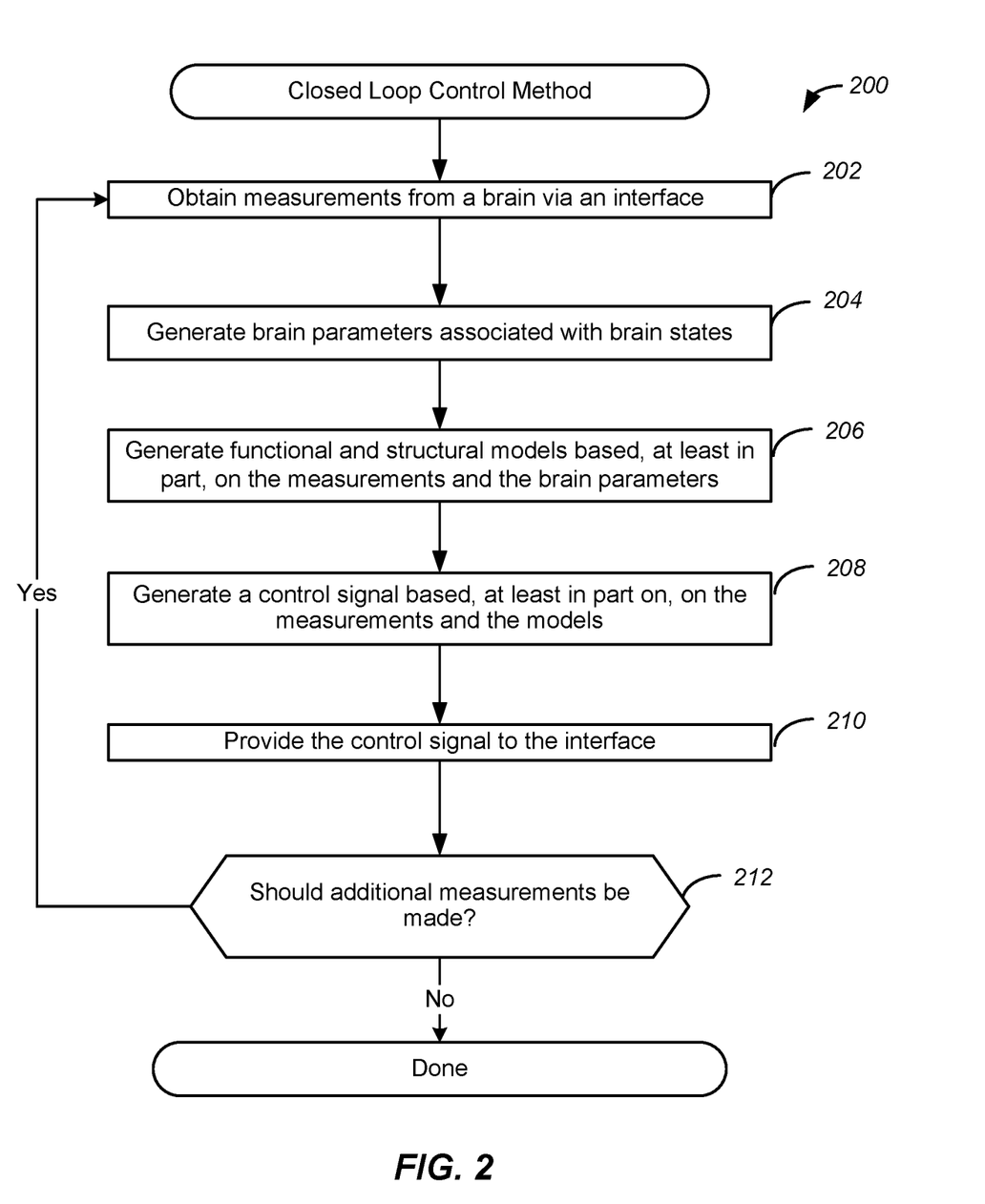
FIG. 2 illustrates an example of a flow chart of a method for providing closed loop control in treatments and cognitive enhancements, implemented in accordance with some embodiments.

FIG. 2 illustrates an example an example of a flow chart of a method for providing closed loop control in treatments and cognitive enhancements, implemented in accordance with some embodiments. As discussed above, various components of system 100 may be configured to implement modeling and closed loop management of treatments and therapies provided to a user.

Accordingly, method 200 may commence with operation 202 during which measurements are obtained from a brain via an interface. The measurements may represent neural activity over a particular period of time, or temporal window, and may be obtained via components of a brain interface. Such measurements may be acquired and stored in a memory.

Method 200 may proceed to operation 204 during which parameters associated with brain states are generated. As similarly discussed above, such parameters may include observers and estimators associated with brain states as well as identification of the brain states themselves. Such parameters may be generated by a first processing device and may be stored in a local memory.

Method 200 may proceed to operation 206 during which functional and structural models are generated based, at least in part, on the measurements and the parameters. As discussed above, such models may emulate functions, tasks, and components of the user's brain, and may be configured based on the brain's activity and behavior. Such models may also be configured based on previously obtained reference data.

Method 200 may proceed to operation 208 during which a control signal is generated based, at least in part on, on the measurements and the models. Accordingly, one or more control signals may be generated based on recent neural activity represented by measurement data, and also based on expected or desired effects as determined based on the models. In this way, specific control signals may be generated to implement a particular cognitive modulation that is specifically configured for the user. Moreover, as discussed above and in greater detail below, such control signals may be generated and implemented in a closed loop manner.

Method 200 may proceed to operation 210 during which the control signal is provided to the interface. Accordingly, the control signal may be provided to the interface which may generate one or more stimuli based on the control signal. For example, such stimuli may include electrical stimuli, visual stimuli, aural stimuli, and/or tactile stimuli that may have parameters, such as amplitude and duration, determined based on the control signal.

Method 200 may proceed to operation 212 during which it may be determined if additional measurements should be made. In various embodiments, such a determination may be made based on a current state, or in response to one or more conditions. For example, if a particular therapeutic regimen is implemented, a series of measurement may be made according to a predetermined schedule, and such measurements may be stepped through utilizing a state machine. If it is determined that additional measurements should be made, method 200 may return to operation 202. If it is determined that no additional measurements should be made, method 200 may terminate.

Figure 3:
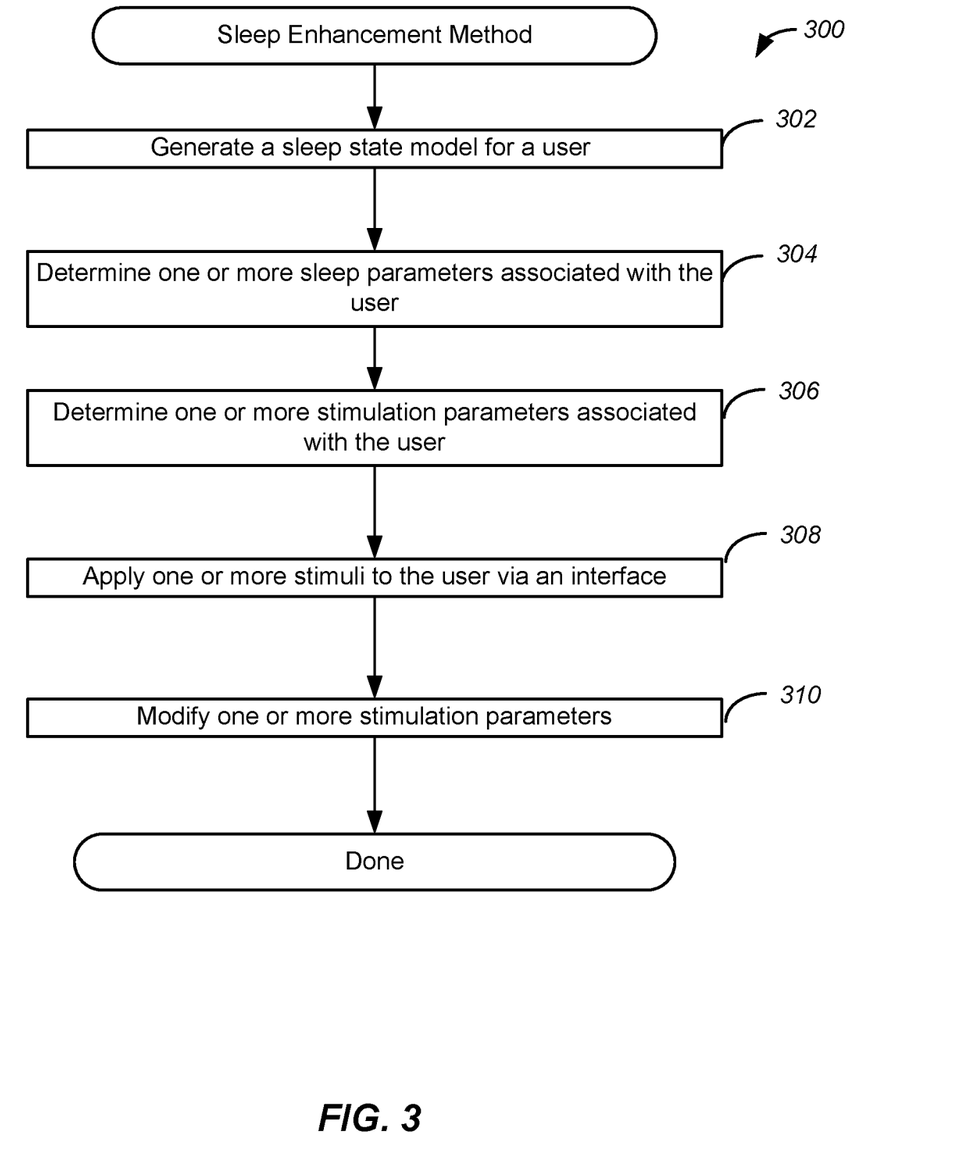
FIG. 3 illustrates an example of a flow chart of a method for providing sleep enhancement, implemented in accordance with some embodiments.

FIG. 3 illustrates a flow chart of a method for providing sleep enhancement, implemented in accordance with some embodiments. As discussed above, various embodiments disclosed herein may provide a system that is configured to receive inputs from a user's brain, generate one or more models, and implement control signals and stimuli based on such models. As also discussed above, the system may be a closed-loop system in which measurements and adjustments are made dynamically and in real-time. As will be discussed in greater detail below, various methods, such as method 300, may be implemented to provide such generation and implementation of control signals and stimuli in the context of sleep enhancement. Accordingly, a closed-loop system and associated methods as described herein may facilitate and enhance a user's path through various stages of sleep. In this way, the user's progression to sleep states is improved, and such improvement is provided in a manner that is customized and dynamically modified based on the user's brain activity.

Method 300 may commence with operation 302 during which a sleep state model may be generated. In various embodiments, the sleep state model may be a computational model that represents a user's brain activity as it relates to one or more sleep stages. As discussed above, the sleep state model may be generated by a processing device, such as a combination of the first and second processing devices. In some embodiments, the first and second processing devices may be implemented as a single processing device. Accordingly, the sleep state model may be configured to map various inputs, which may be received measurements and other data inputs, to particular sleep states or stages of a user. As will be discussed in greater detail below, a user may experience many stages of sleep when sleeping, and the advancement and progression of the user through such stages may be related to the quality of the user's sleep. The sleep state model may be used to identify and develop an optimal path or profile for the user that lays out optimal transitions through the different sleep stages as a target.

In some embodiments, the user may have several stages of sleep, such as a first stage of sleep, a second stage of sleep, a third stage of sleep, a fourth stage of sleep, and rapid eye movement (REM) sleep. Accordingly, such stages may be non-rapid eye movement (NREM) sleep stages 1-4 (where 3 and 4 are known as slow wave, or deep sleep), and may be rapid eye movement sleep (REM; named because of the eye movements that phasically occur during this stage of sleep). Accordingly, the sleep state model may include data values that identify measurements of a user's brain activity that correspond to each sleep stage. In this way, the sleep state model is configured to determine a user's sleep stage based on one or more received measurements. As will be discussed in greater detail below, each sleep stage of the sleep state model may be represented by data values that identify frequency ranges and patterns of activity, such as a frequency range and period of oscillation of neural activity. Moreover, the values of the frequency ranges and patterns of activity may be predetermined based on a set of default values, or may be determined during a learning and observation phase.

The sleep state model may be generated by a system component, such as a processing device, and may be generated based on observed data. For example, during a training or observation period, measurements may be made by electrodes, and the controller may record the measurements. Such an observation period may be a period of sleep for the user in which measurements are made while the user is progressing through different stages of sleep. The processing device may map the measurements to particular stages of sleep, and the mapping may be stored as part of the sleep state model. In various embodiments, the sleep state model may also store power spectra of neural activity and shifts in power spectra that are associated with transitions between sleep stages. In this way, the sleep state model may store data that identifies particular neural activity, such as shifts in power spectra, that occur when the user transitions from one state to another. As will be discussed in greater detail below, one or more machine learning algorithms may be utilized to generate inputs, such as estimated stimuli, that may achieve a particular output, such as a target sleep stage.

In various embodiments, the measurements may include respiration, heart rate, electrooculography (EOG), temperature, body movements, oximetry measurements to estimate the sleep stage model. The sleep state model could estimate the stage of sleep a user is in, the spectral activity in the different sleep stages, the transition propensity for the user to move from one stage to another. In some embodiments, some sleep stage transitions being beneficial like transition from a lighter sleep stage to a deeper sleep stage, while other state transitions being detrimental like a transition from sleep stage 1 to wake or sleep stage 2 to wake (at certain level of propensity, these transitions can be an indicator of insomnia). The sleep state model may also be configured to estimate attributes of sleep including the latency and duration of the various sleep stages. The temporal and spectral patterns of the above measurements can directly be used to estimate these sleep state models, or it could include estimates and observers that develop estimates of the sleep state based on the measurements.

Method 300 may proceed to operation 304 during which one or more sleep parameters may be determined. In various embodiments, the sleep parameters may be parameters that are used to identify a user's sleep stage. As discussed above, a user may have various different sleep stages that are each characterized by different brain activities and physiological behaviors. During operation 304 one or more sleep parameters may be identified based on measurements received via an interface. For example, received measurements may include a frequency and oscillatory behavior of neural activity of a user, and such measurements may be used to identify particular sleep parameters, such as the presence or absence of slow wave delta waves as well as faster brain waves that have faster frequencies.

Method 300 may proceed to operation 306 during which one or more stimulation parameters may be generated. In various embodiments, the stimulation parameters may be parameters that are configured to provide the user with a stimulus that facilitates the advancement of the user to a next stage of sleep. In various embodiments, the stimulation parameters may be configured to retain a user in a deep stage of sleep to provide improved restorative benefits. Thus, the sleep parameters may be used in conjunction with the sleep state model to identify a current sleep stage of the user. Then, a system component, such as the controller, may identify one or more stimuli that will transition the user to the next stage of sleep or retain the user in a particular stage of sleep for longer. Stimulation parameters may be parameters such as a type of modality, a strength of stimulation, a frequency range of stimulation, duration of stimulation, and a site of stimulation. In various embodiments, the stimulation parameters may be modulated based on an amount of added randomization to prevent habituation by the user. For example, a stimulation frequency may be randomly increased or decreased by a particular amount to avoid a user becoming habituated to that frequency of stimulation. In some embodiments, the appropriate stimuli may have been previously determined and stored as part of the sleep state model. Accordingly, during operation 306, the stimulation parameters may be retrieved from the sleep state model.

Method 300 may proceed to operation 308 during which the one or more stimuli may be applied based, at least in part, on the stimulation parameters. As discussed above, such stimuli may be applied via one or more interfaces. For example, the stimuli may be electrical stimuli that are applied via electrodes included in the interface. In some embodiments, the stimulating may include applied electrical stimulation at a sleep frequency (for example, a slow wave regime having frequencies of 0-0.5 or 0-1 Hz, in a delta band 1-4 Hz, in a theta band 4-8 Hz or in an alpha band 8-12 Hz). The stimulating may include applied electrical stimulation at higher frequencies (for depth stimulation and for reducing stimulation sensation and side effects), while also stimulating at the sleep frequency as a beat frequency of the higher frequencies (for example: 995 Hz and 1000 Hz at lateral locations to create a 5 Hz stimulation beat frequency). As will be discussed in greater detail below with reference to FIG. 4, the stimuli may also be applied via one or more additional modalities as well.

As will be discussed in greater detail below, the determination and the application of the stimuli is configured to aid a user when transitioning between stages of sleep. For example, if a dominant rhythm of particular stage of sleep is identified, the stimulation may guide the user to the next stage. As noted above, stages may be represented by frequency ranges and patterns of activity. More specifically, if the precursor to the first stage N1 is identified, such a first drowsy light sleep stage may be dominated by alpha 8-12 Hz activity, and the next stages N1 and N2 may be known to be dominated by theta 4-8 Hz activity, while N2 will have additional spindle band 12-16 Hz and a third stage N3 may be dominated by delta and slow wave activity. Accordingly, application of stimuli may be configured to apply stimuli associated with a target sleep stage to promote transition from the current sleep stage. Accordingly, stimulation at 10 Hz may make the user drowsy and get to stage N1 faster. Furthermore, when in N1, stimulation may be applied at 5 Hz and could help guide the user to N2 faster. Further still, when in N2, stimulation could be applied at 1 Hz and could guide the user to N3 faster. In this way, the stimulation parameters may be determined and applied to affect the onset and durations of sleep stages.

Moreover, as will be discussed in greater detail below, combinations of different stimulation modalities may be used to transition the user between stages of sleep. For example, transcranial electrical stimulation could be applied for all transitions, or transcranial electrical stimulation could be applied before sleep, then a combination of auditory and transcranial electrical stimulation could be applied in N1, and just auditory stimulation could be applied in subsequent stages, such as N3.

Method 300 may proceed to operation 310 during which one or more stimulation parameters may be modified. Accordingly, the system may continue to monitor the user and determine if additional stimulation parameters should be generated to further facilitate the user transitioning between sleep stages. For example, it may be determined that additional stimuli should be provided to continue aiding in a transition between stages. In another example, a transition between stages may have been completed, and it may now be determined if an additional transition should be implemented. In another embodiment, the stimulation frequencies can be sequenced at the beginning for various durations to facilitate efficient and faster transitions to the later sleep stages, and not wait to stimulate at the different sleep stages. Additional details regarding such modifications of parameters are discussed in greater detail below with reference to FIG. 4. While many of the above operations have been described with reference to a user's sleep cycle, it will be appreciated that many of the operations described above may be implemented before, after, and/or during sleep. For example, measurements may be made and stimuli may be applied before, after, and/or during sleep.

Figure 4:
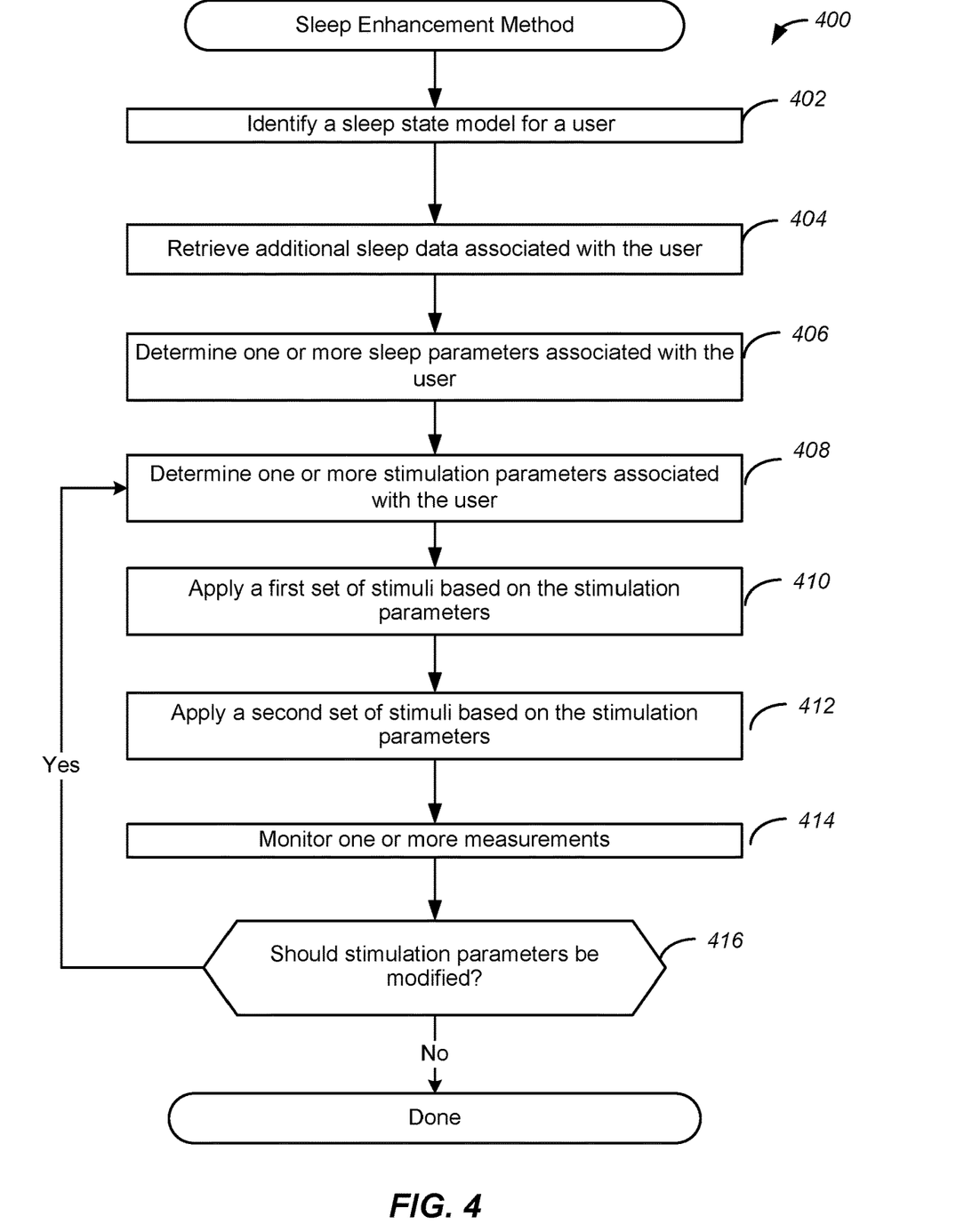
FIG. 4 illustrates an example of a flow chart of another method for providing sleep enhancement, implemented in accordance with some embodiments.

FIG. 4 illustrates a flow chart of another method for providing sleep enhancement, implemented in accordance with some embodiments. As discussed above, various embodiments disclosed herein may provide a system that is configured to receive inputs from a user's brain, generate one or more models, and implement control signals and stimuli based on such models. As also discussed above, the system may be a closed-loop system in which measurements and adjustments are made dynamically and in real-time. As will be discussed in greater detail below, various methods, such as method 400, may be implemented to provide such generation and implementation of control signals and stimuli in the context of sleep enhancement. Furthermore, additional sources of data and information may be utilized, as well as various different stimulation modalities. In this way, the customized and dynamically modified control signals and stimuli may be generated from a diverse range of information, and various different stimuli may be implemented based on such diverse information.

Method 400 may commence with operation 402 during which a sleep state model may be identified. As discussed above, the sleep state model may be a computational model that represents a user's brain activity as it relates to one or more sleep stages. Accordingly, the sleep state model may be configured to map various inputs, which may be received measurements and other data inputs, to particular sleep states or stages of a user. Accordingly, during operation 402, a user's sleep state model may be retrieved from memory, such as a storage device. In some embodiments, if no previous sleep state model is available, a training or observation period may be implemented, and a sleep state model may be generated.

Method 400 may proceed to operation 404 during which during which additional sleep data may be retrieved. In some embodiments, sleep data may be obtained from various different data sources, such as wearable smart devices and other fitness tracking devices. In various embodiments, the additional data may be obtained from an application implemented on the user's smart device, such as a smart phone, that may include heart rate measurements. Accordingly, such data may store additional physiological data of the user, and may be retrieved from those devices and aggregated with the existing data stored by a system component, such as a controller. The aggregated data may be used in adapting or enhancing the sleep state model for the user.

Method 400 may proceed to operation 406 during which one or more sleep parameters may be identified. As discussed above, the sleep parameters may be parameters that are used to identify a user's sleep stage, where each stage is characterized by different brain activities and physiological behaviors. Accordingly, during operation 406 one or more sleep parameters may be identified based on measurements received via an interface. Furthermore, such sleep parameters may be identified based on the retrieved additional data as well. Accordingly, additional data may be retrieved from smart wearable devices during a period of observation, and may be combined with measurements received from components of an interface, such as electrodes. The combined data may form the basis of the identification of particular sleep parameters. As previously discussed above, sleep parameters may characterize neural and physiological activity, such as the presence or absence of slow wave delta waves as well as faster brain waves that have faster frequencies. The sleep parameters could be estimates of the latency or duration of specific sleep stages.

Method 400 may proceed to operation 408 during which one or more stimulation parameters may be generated. As similarly discussed above, the stimulation parameters may be parameters that are configured to provide the user with a stimulus that facilitates the advancement of the user to a next stage of sleep. Accordingly, during operation 408, the sleep parameters may be used in conjunction with the sleep state model to identify a current sleep stage of the user. Then, a system component, such as the controller, may identify one or more stimuli that will transition the user to the next stage of sleep.

Method 400 may proceed to operation 410 during which a first set of stimuli may be applied based, at least in part, on the stimulation parameters. As discussed above, such stimuli may be applied via one or more interfaces. For example, the stimuli may be electrical stimuli that are applied via electrodes included in the interface. Accordingly, during operation 410, one or more electrical stimuli may be applied via one or more electrodes.

Method 400 may proceed to operation 412 during which a second set of stimuli may be applied based, at least in part, on the stimulation parameters. As discussed above, stimuli may be applied via one or more additional modalities. For example, stimuli may be audio stimuli, tactile stimuli, and/or vibratory stimuli. It will be appreciated that combinations of different modalities may be implemented as well. In one example, physical stimuli, such as movement or rocking of the user's bed or sleep environment, may be applied during operation 412. For example, particular components of the user's bed and sleep environment, such as the mattress, pillow, or head band, may be rocked. In some embodiments, such components may be configured to have contours that when oscillated, create a rocking sensation. In some embodiments, auditory stimuli may be provided at frequencies that interact with the user's cochlea and give the user a rocking sensation without actual physical rocking. In this way, a combination of multiple different stimulation modalities may be controlled and applied based on the user's current sleep stage as well as the information included in the user's sleep state model.

Method 400 may proceed to operation 414 during which one or more measurements may be monitored. Accordingly, after the sets of stimuli have been applied, the user may be monitored and measurements may be made to identify what effect the stimuli had. Thus, during operation 414, additional measurement data may be collected via components of an interface, such as electrodes, as well as any available wearable devices and/or fitness trackers.

Method 400 may proceed to operation 416 during which it may be determined if the stimulation parameters should be modified. Such a determination may be made based on the user's sleep state model. For example, the measurements obtained during operation 414 may indicate that the user has begun transitioning from one sleep stage to another, and the sleep state model may indicate that additional stimuli should be applied. In another example, the measurements obtained during operation 414 may indicate that the user has completed the transition to another sleep stage and no additional stimuli should be applied. If it is determined that the stimulation parameters should be modified, method 400 may return to operation 408. If it is determined that the stimulation parameters should not be modified, method 400 may terminate.

Figure 5:
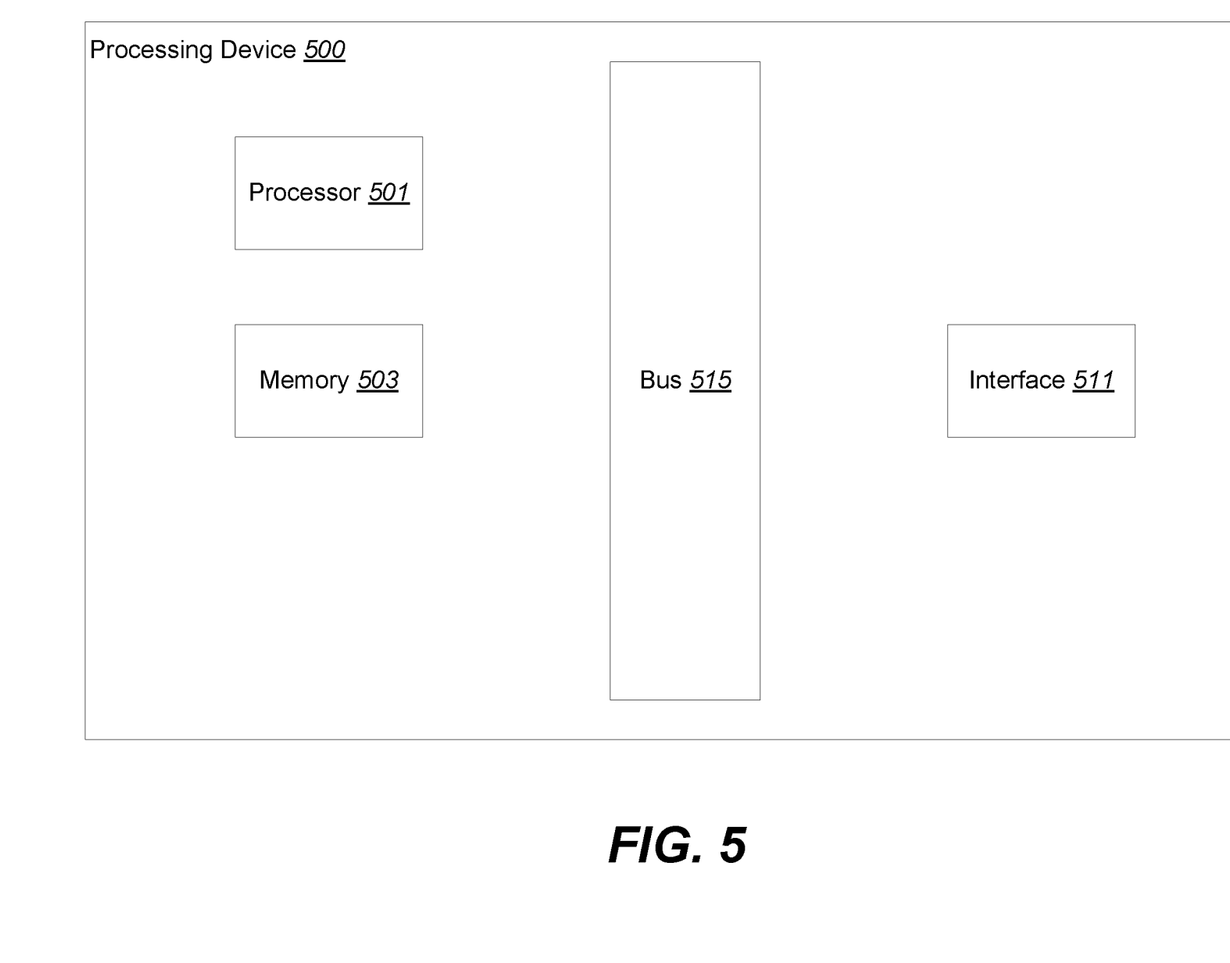
FIG. 5 illustrates an example of a processing device that can be used with various embodiments.

FIG. 5 illustrates an example of a processing device that can be used with various embodiments. For instance, the processing device 500 can be used to implement any of first processing device 104, second processing device 106, and/or controller 108 according to various embodiments described above. In addition, the processing device 500 shown can be implemented in conjunction with a computing system on a mobile device or on a computer or laptop, etc. According to particular example embodiments, a processing device 500 suitable for implementing particular embodiments of the present invention includes a processor 501, a memory 503, an interface 511, and a bus 515 (e.g., a PCI bus). The interface 511 may include separate input and output interfaces, or may be a unified interface supporting both operations. When acting under the control of appropriate software or firmware, the processor 501 is responsible for tasks such as closed loop control. Various specially configured devices can also be used in place of a processor 501 or in addition to processor 501. The complete implementation can also be done in custom hardware. The interface 511 may be configured to send and receive data packets or data segments over a network. Particular examples of interfaces the device supports include Ethernet interfaces, frame relay interfaces, cable interfaces, DSL interfaces, token ring interfaces, and the like. In various embodiments, interface 511 may also be a wired connection or a bus with appropriate communications ports.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the processing device 500 uses memory 503 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present invention relates to tangible, machine readable media that include program instructions, state information, etc. for performing various operations described herein. Examples of machine-readable media include memory devices such as non-volatile memory devices, volatile memory devices, and may also utilize optical media such as CD-ROM disks and DVDs, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the invention. Specifically, there are many alternative ways of implementing the processes, systems, and apparatuses described. It is therefore intended that the invention be interpreted to include all variations and equivalents that fall within the true spirit and scope of the present invention. Moreover, although particular features have been described as part of each example, any combination of these features or additions of other features are intended to be included within the scope of this disclosure. Accordingly, the embodiments described herein are to be considered as illustrative and not restrictive.

What is claimed is:

1. A system comprising:
    a plurality of electrodes configured to be coupled to a brain of a user and configured to obtain a plurality of measurements from the brain of the user;
    an interface configured to obtain the plurality of measurements from the plurality of electrodes;
    one or more processors configured to generate a sleep state model associated with the user, the sleep state model identifying characteristics of a plurality of sleep stages, and further identifying characteristics of transitions between the plurality of sleep stages; and
    the one or more processors configured to generate a control signal based on the sleep state model and the plurality of measurements;
    wherein the control signal is configured to initiate a change in a current sleep stage of the user via application of first electrical stimuli to the brain, wherein the transitions between the plurality of sleep stages comprises a transition from the current sleep stage to a second sleep stage, wherein the current sleep stage can comprise one of N1, N2, N3 or REM sleep stages, and wherein to change the current sleep stage of the user, the control signal is further configured to, in response to determining that the user is beginning the transition from the current sleep stage to the second sleep stage, apply additional electrical stimuli to the brain.

2. The system of claim 1, wherein the interface comprises the plurality of electrodes, and wherein the plurality of measurements is neural activity of the user.

3. The system of claim 2, wherein the control signal comprises a plurality of stimuli generated based on a plurality of stimulation parameters.

4. The system of claim 3, wherein the controller is further configured to provide the control signal to the brain via the interface and the plurality of electrodes.

5. The system of claim 4, wherein the plurality of sleep stages is identified based, at least in part, on the plurality of measurements obtained from the user, and wherein the plurality of stimulation parameters is determined based on the sleep state model.

6. The system of claim 1, wherein the control signal includes a plurality of electrical stimuli applied via the plurality of electrodes.

7. The system of claim 1, wherein the control signal includes a plurality of auditory or tactile stimuli applied via a sleep environment of the user.

8. A device comprising:
an interface configured to obtain a plurality of measurements from a brain of a user;
one or more processors configured to generate a sleep state model associated with the user, the sleep state model identifying characteristics of a plurality of sleep stages, and further identifying characteristics of transitions between the plurality of sleep stages; and
the one or more processors configured to generate a control signal based on the sleep state model and the plurality of measurements;
wherein the control signal is configured to initiate a change in a current sleep stage of the user via application of first electrical stimuli to the brain, wherein the transitions between the plurality of sleep stages comprises a transition from the current sleep stage to a second sleep stage, wherein the current sleep stage can comprise one of N1, N2, N3 or REM sleep stages, and wherein to change the current sleep stage of the user, the control signal is further configured to, in response to determining that the user is beginning the transition from the current sleep stage to the second sleep stage, apply additional electrical stimuli to the brain.

9. The device of claim 8, wherein the interface comprises a plurality of electrodes, and wherein the plurality of measurements is neural activity of the user.

10. The device of claim 9, wherein the control signal comprises a plurality of stimuli generated based on a plurality of stimulation parameters, and wherein the controller is further configured to provide the control signal to the brain via the interface and the plurality of electrodes.

11. The device of claim 10, wherein the plurality of sleep stages is identified based, at least in part, on the plurality of measurements obtained from the user, and wherein the plurality of stimulation parameters is determined based on the sleep state model.

12. A method comprising:
receiving, via an interface coupled to a brain of a user, a plurality of measurements from the user;
identifying, using one or more processors of a processing device, based, at least in part, on the plurality of measurements, a plurality of sleep stages of the user; and
generating, using one or more processors of the processing device, a sleep state model associated with the user, the sleep state model identifying characteristics of each of the plurality of sleep stages, and further identifying characteristics of transitions between the plurality of sleep stages;
generating, using one or more processors of a controller, a control signal based on the sleep state model and the plurality of measurements, wherein the control signal changes a current sleep state of the user, and wherein the plurality of sleep stages comprises a first stage of sleep, a second stage of sleep, a third stage of sleep, a fourth stage of sleep, and rapid eye movement (REM) sleep;
wherein the control signal is configured to initiate a change in a current sleep stage of the user via application of first electrical stimuli to the brain, wherein the transitions between the plurality of sleep stages comprises a transition from the current sleep stage to a second sleep stage, wherein the current sleep stage can comprise one of N1, N2, N3 or REM sleep stages, and wherein to change the current sleep stage of the user, the control signal is further configured to, in response to determining that the user is beginning the transition from the current sleep stage to the second sleep stage, apply additional electrical stimuli to the brain.

13. The method of claim 12, wherein the interface comprises a plurality of electrodes, wherein the plurality of measurements is neural activity of the user, wherein the control signal comprises a plurality of stimuli generated based on a plurality of stimulation parameters, and wherein the controller is further configured to provide the control signal to the brain via the interface and the plurality of electrodes.

14. The method of claim 13, wherein the plurality of sleep stages is identified based, at least in part, on the plurality of measurements obtained from the user, and wherein the plurality of stimulation parameters is determined based on the sleep state model.

15. The method of claim 13, wherein the control signal includes a plurality of electrical stimuli applied via a plurality of electrodes.

16. The method of claim 13, wherein the control signal includes a plurality of auditory or tactile stimuli applied via a sleep environment of the user.

17. The system of claim 1, wherein the second stage is a deeper sleep stage than the current stage.

* * * * *